United States Patent [19]

Ligorati et al.

[11] 4,339,605
[45] Jul. 13, 1982

[54] PROCESS FOR THE THERMAL DECOMPOSITION OF PHENOL PITCH

[75] Inventors: Ferdinando Ligorati, Usmate; Emanuele Sartorio, Messina, both of Italy

[73] Assignee: Euteco Impianti S.p.A., Milan, Italy

[21] Appl. No.: 119,720

[22] Filed: Feb. 8, 1980

[51] Int. Cl.$^3$ ............................................. C07C 45/51
[52] U.S. Cl. .................................... 568/383; 568/754; 585/437; 585/469; 203/91
[58] Field of Search ............... 568/383, 401, 754, 749, 568/761; 585/435, 410, 437, 469; 203/91

[56] References Cited

U.S. PATENT DOCUMENTS

| | | | |
|---|---|---|---|
| 2,992,169 | 7/1961 | Gregory et al. | 568/754 |
| 3,215,745 | 11/1965 | Frank | 568/754 |
| 3,631,214 | 12/1971 | Engelbrecht et al. | 585/439 |
| 3,850,996 | 11/1974 | Nixon | 568/754 |

OTHER PUBLICATIONS

Kolesnikov et al., Chem. Abst., vol. 88, #74201e, (1978).
Takahashi et al., Chem. Abst., vol. 89, #163263q, (1978).
Bartkowiak et al., Chem. Abst., vol. 85, #46195a, (1976).

*Primary Examiner*—Natalie Trousof
*Assistant Examiner*—James H. Reamer
*Attorney, Agent, or Firm*—Sughrue, Mion, Zinn, Macpeak & Seas

[57] ABSTRACT

Phenol pitch obtained as a bottoms fraction in the distillation of phenol deriving from the acid hydrolysis of cumene hydroperoxide is treated to recover therefrom desired products consisting of phenol, alpha-methylstyrene, cumene and acetone, by introducing steam and the phenol pitch, into a reactor in a weight ratio of from 0.01:1 to 1:1, withdrawing from the top of said reactor a vapor phase comprising said desired products, withdrawing from the bottom of said reactor a liquid phase consisting essentially of compounds of higher boiling point than said desired products, and operating at a pressure of 4–12 Kg/cm$^2$, at a temperature of 320°–400° C., as measured in the liquid phase, and with a residence time of 0.5–10 hours.

5 Claims, No Drawings

PROCESS FOR THE THERMAL DECOMPOSITION OF PHENOL PITCH

The present invention relates to a process for the pyrolysis of mixtures obtained as a bottoms fraction in the distillation of phenol deriving from the acid hydrolysis of cumene hydroperoxide.

As is known, in the commercial process for the production of phenol and acetone via cumene hydroperoxide, cumene is oxidized to cumene hydroperoxide, and the hydroperoxide is subjected to hydrolysis in an acid medium, whereby there is obtained a complex liquid mixture comprising acetone and phenol. This hydrolysis mixture is separated by rectification into a light fraction consisting of raw acetone and a heavy fraction consisting of raw phenol. The phenol fraction is separated by rectification into a overhead product consisting of phenol and a bottoms fraction comprising the heavy by-products formed during the various steps of the process.

The hydrolysis of cumene hydroperoxide is accompanied by secondary reactions which lead to the formation of various by-products, such as acetophenone and phenyl dimethylcarbinol. The acid hydrolysis medium facilitates hydration of phenyl dimethylcarbinol to alpha-methylstyrene, which may react with itself to form dimers of various structures, or else with phenol to form ortho-or paracumyl phenol. These secondary reactions are accompanied by others, which are promoted not only by the acidity, but also by the high temperatures used in the reboilers of the fractional distillation columns. There is thus obtained a large number of compounds having also a high molecular weight and predominantly of a pitchy nature.

The said distillation residue, commonly referred to as the phenol pitch, is a non-negligible fraction amounting to about 10–15% by weight of the phenol produced. It is thus obvious that the treatment of the phenol pitch to recover from the latter the highest possible quantity of useful products which can be recycled to the process, has a direct influence on the economics of said process.

In the known art the phenol pitch is usually submitted to thermal decomposition treatments, mainly to convert the cumyl phenols and the dimers of alpha-methylstyrene into phenol, alpha-methylstyrene monomer and cumene. The mixture obtained by pyrolysis of said pitch is separated by distillation into useful products and a bottoms fraction consisting of tars.

The operating conditions used in the known art for said thermal decomposition do not afford satisfactory yields of phenol, alpha-methylstyrene and cumene with respect to the stoichiometrical values calculated on the basis of the cumyl phenols and the dimers of alpha-methylstyrene present in the phenol pitch. In order to increase these yields, use is made in the known art of catalytic agents, by carrying out said pyrolysis in the presence of acid compounds as catalysts.

In addition to the difficulty in achieving sufficiently high yields, pyrolysis of phenol pitch presents also serious problems of a technical nature, deriving from the high viscosity of the distillation residue of the pyrolyzed phenol pitch. This high viscosity, in fact, makes extremely difficult, and in some cases impossible, the removal of said residue from the apparatus through the discharge pipes.

The above drawbacks, inherent to the thermal decomposition processes of phenol pitch according to the known art, are overcome by means of the process of the present invention, which permits the recovery yields of the desired pyrolysis products, such as phenol, alpha-methylstyrene and cumene, to be noticeably increased while permitting acetone to be recovered as a useful product from said pitch and yielding also, upon separation of said useful products, a pyrolysis residue with a low solidification point, of sufficient fluidity and easy to remove.

These surprising results are achieved by carrying out the thermal decomposition of phenol pitch under particular operating conditions, including as a specific condition the presence of water in the reaction mixture and the application of a superatmospheric pressure.

According to the invention, there is provided a continuous process for treating the phenol pitch obtained as a bottoms fraction in the distillation of raw phenol deriving from the acid hydrolysis of cumene hydroperoxide, to recover therefrom desired products consisting of phenol, alpha-methylstyrene, cumene and acetone, which comprises introducing said phenol pitch, preheated to a temperature of from 180° C. to 280° C., and steam into a reactor in a weight ratio between steam and phenol pitch of from 0.01:1 to 1:1, withdrawing from the top of said reactor a vapor phase comprising said desired products, the latter being obtained by thermal decomposition of said phenol pitch or being initially present in the pitch, withdrawing from the bottom of said reactor a liquid phase consisting essentially of compounds with a higher boiling point than said desired products, said compounds being obtained by thermal decomposition of said phenol pitch or being initially present in the latter, and operating in the reactor at a pressure of from 4 to 12 Kg/cm$^2$, at a temperature of from 320° to 400° C., as measured in said liquid phase, and with an average residence time of the phenol pitch in the reactor of from 0.5 to 10 hours.

The thermal decomposition of phenol pitch according to the process of the invention may be carried out in a reactor, possibly provided at its upper end with a droplet-capturing column, the said pitch and the steam being delivered to an intermediate level of said reactor, the useful products, together with the steam, being discharged from the top and the residue consisting of the undesired compounds being discharged in the liquid phase from the bottom.

The said liquid phase occupies the lower zone of the reactor up to a pre-determined level, which is maintained constant during the pyrolysis, whereas the upper zone of the reactor is occupied by said vapor phase.

The vapors recovered from the top of the reactor, upon condensation, separate into an aqueous phase and an organic phase, the latter comprising the useful products thus recovered.

In the industrial practice, however, it is more convenient to use for said thermal decomposition, instead of a generic reactor, a distillation column in which there are carried out simultaneously the pyrolysis reaction and the separation by rectification of the desired products from the undesired compounds. In this case, the phenol pitch and the steam are delivered to an intermediate zone of the distillation column, thus obtaining the desired products as an overhead product and the undesired compounds as a bottoms fraction.

The use of a distillation column for the thermal decomposition of phenol pitch offers obvious advantages, consisting in the achievement of a better separation of the desired products from the undesired compounds, and the obtaining of said desired products with a higher degree of purity. In particular, by using a distillation column, it is possible to separate to a higher extent acetophenone from the overhead product, and thus to enrich in acetophenone the bottoms fraction, thereby increasing the degree of fluidity of said fraction and lowering its solidification point.

The use of water in the thermal decomposition of phenol pitch, together with the other operating conditions used, affords very surprising results. The presence of water, fed to the reactor in the vapor phase together with the phenol pitch, brings about a noticeable increase in the recovery yield of phenol, alpha-methylstyrene, cumene and acetone, and also a drastic decrease in viscosity and solidification point of the pyrolysis residue.

In particular, the sum of the yields of alpha-methylstyrene and cumene is noticeably higher than 100% with respect to the stoichiometrical value based on the overall quantity of cumyl phenols, dimers of alpha-methylstyrene and phenyl dimethylcarbinol initially present in the phenol pitch. This surprising increase in yield can only be explained by admitting the presence in the phenol pitch of compounds different from cumyl phenols, dimers of alphamethylstyrene and phenyl dimethylcarbinol, which under the specific influence of water act as precursors, thus yielding alpha-methylstyrene and cumene. Moreover, the obtaining of a bottoms fraction with a high degree of fluidity and a low solidification point, is obviously of a great advantage. In fact, with such characteristics, the technical problems relating to the removal of said fraction from the apparatus through the discharge pipes, become greatly simplified.

The influence of water on the pyrolysis of phenol pitch derives from its envolvement in chemical reactions and thermodynamic equilibrii which would be difficult to fully explain.

However, it may be assumed on the basis of the experimental data obtained, that water, under the conditions used for said pyrolysis, promotes decomposition of highboiling compounds of various structures, which otherwise could not be recovered, with production of cumene and alpha-methylstyrene.

It may also be assumed, still on the basis of experimental results, that water also has an inhibiting action on the formation of carbonaceous products. Most probably, water is involved in the condensation reactions, thus shifting the equilibrium of these reactions and inhibiting the formation of condensation products. Among these last reactions, the autocondensation reactions of acetophenone, which may lead to the formation of different compounds, such as dypnone and 1, 3, 5-triphenylbenzene, are of great importance during pyrolysis of phenol pitch. The water, by drastically limiting the formation of said autocondensation products, permits the concentration of acetophenone in the pyrolysis medium to be maintained at high values. The presence of acetophenone noticeably contributes to reducing the viscosity and the solidification point of the pyrolysis residue.

Another reaction in which water is involved, thus allowing the recovery of a valued product which could not be recovered otherwise, is the decomposition of mesityl oxide or of precursors of the latter usually present in phenol pitch, which leads to the formation of acetone according to the following reaction:

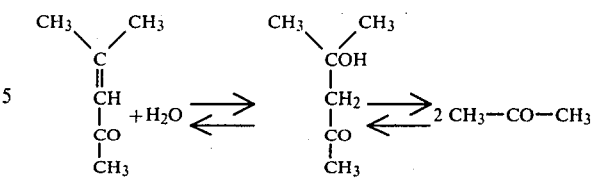

As regards the feedings of the reactor, it has been experimentally ascertained that the weight ratios between water and phenol pitch yielding best results are generally from 0.01:1 to 1:1, the preferred values ranging from 0.04:1 to 0.2:1. When using lower ratios, the amount of water is insufficient to fully achieve the desired effect, whereas with higher ratios the water is present in useless excess, which adversely affects the economics of the process.

Carrying out the pyrolysis of phenol pitch under pressure is an essential feature of the process of the present invention. In fact, the operating pressure is a parameter which has a fundamental influence on the course of said pyrolysis. The interpretation of the influence of the pressure on the pyrolysis is very complex, as the thermodynamical equilibrii involved which depend on said pressure, are numerous and interconnected.

In particular the pressure is of fundamental importance to depress the formation of the phenol-acetophenone azeotrope, thus permitting the acetophenone to remain at least in part in the pyrolysis residue present in the reactor as a liquid phase. The presence of acetophenone in said residue contributes to a fundamental extent to reducing the viscosity and the solidification point. The experimental data confirm that the carrying out of the pyrolysis of phenol pitch under superatmospheric pressure leads to markedly improved results with respect to the use of atmospheric pressure.

The pressure is conveniently maintained at values of from 4 kg/cm$^2$ to 12 kg/cm$^2$, values of from 6 kg/cm$^2$ to 9 kg/cm$^2$ being preferred. When operating at lower pressure values, the depressing effect on the formation of the phenolacetophenone azeotrope is excessively reduced, whereas the use of higher values brings about technical problems linked to the use of high pressure, which would bear on the economics without being compensated for by further improvements in the results.

The thermal decomposition of phenol pitch according to the present invention may be carried out at a temperature of from 320° C. to 400° C., this temperature being measured in the liquid phase present in the reactor. Best results are generally obtained by operating at a temperature of from 335° C. to 370° C.

The average residence time of the phenol pitch in the reactor depends on the pyrolysis temperature. In fact, when using low temperatures, the residence times must be higher, whereas shorter residence times are sufficient when using higher temperatures. In general, the said residence time conveniently is from 0.5 to 10 hours, values of from 1 to 4 hours being generally preferred.

When using pyrolysis temperatures lower than 320° C., the velocity of the reactions occurring during thermal decomposition of the phenol pitch, is too low. With residence times in the reactor lower than 0.5 hours the said pyrolysis reactions are not brought to completion. The use of temperatures and residence times higher than the limits indicated above fosters undesired reactions which lead to the formation of carbonaceous compounds.

When operating under the aforesaid conditions, the process of the present invention permits the thermal decomposition of phenol pitch to be carried out with a phenol yield higher than 90% with respect to the stoichiometrical value calculated on the basis of the cumyl phenols initially present in said pitch, and with a yield of the sum of cumene and alpha-methylstyrene higher than 100% with respect to the stoichiometrical value calculated on the basis of the cumyl phenols, dimers of alpha-methylstyrene and phenyl dimethylcarbinol initially present in said pitch. The process of the invention makes also possible the recovery of acetone from the mesityl oxide and the precursors thereof present in the phenol pitch.

The process of the present invention allows also the recovery as a pyrolysis residue, upon separation from the useful products, of a mixture having a low solidification point, generally lower than 100° C., and a high degree of fluidity, so that said residue can be easily removed from the apparatus through the discharge pipes.

EXAMPLE 1

There is used an apparatus comprising a reactor of 500 cc capacity, provided at its upper end with a droplet-capturing column having a height of 200 mm and a diameter of 25 mm, filled with Fenske rings 5 mm in diameter.

The composition of the phenol pitch used in this example, expressed in weight percent, is shown in Table 1.

To an intermediate zone of the reactor there are delivered the said phenol pitch, heated to 200° C., at a rate of 125 g/hour, and steam at a rate of 6.6 g/hour. The weight ratio between steam and phenol pitch in the feed is 0.053:1.

The reactor is operated at a temperature of 345° C., as measured in the liquid phase, and at a pressure of 8 kg/cm$^2$. The vapor phase is discharged from the top of the reactor through the droplet-capturing column, whereas the liquid phase is discharged from the bottom of the reactor, while maintaining the volume of said liquid phase in the reactor at a constant value of 250 cc by controlling the level.

The average residence time of the phenol pitch in the reactor is 2 hours. The weight ratio between vapor phase and liquid phase discharged is 2.76:1.

The vapors discharged from the top of the reactor, upon cooling and condensation, separate into an organic phase and an aqueous phase. The organic base, consisting of the mixture of useful products recovered, amounts to 72% by weight with respect to the feed of phenol pitch. The composition in weight percent of the mixture of recovered products is shown in Table 1.

The recovery yield of phenol is 90.5% with respect to the stoichiometrical value calculated on the basis of the cumyl phenols present in the feed of phenol pitch.

The sum of the recovery yields of cumene and alpha-methylstyrene is 109.2% with respect to the stoichiometrical value calculated on the basis of the cumyl phenols, dimers of alpha-methylstyrene and phenyl dimethylcarbinol present in the phenol pitch fed in.

The liquid discharged from the bottom of the reactor, which constitutes the pyrolysis residue containing the undesired compounds, amounts to 28% by weight of the phenol pitch fed in. The composition in weight percent of said pyrolysis residue is shown in Table 1.

The pyrolysis residue has a solidification point of 95° C., a sufficient fluidity and is easy to remove.

EXAMPLE 2 (Comparative)

In this Example, the thermal decomposition of the phenol pitch is carried out in the absence of water.

There is used the apparatus of Example 1. The phenol pitch has the same composition as in Example 1, said composition being shown in Table 1. The other operating conditions, excepting the feeding of water, are identical to those used in Example 1.

The mixture of useful products recovered amounts to 64% by weight with respect to the phenol pitch fed in. The composition in weight percent of this mixture is shown in Table 1. The recovery yield of phenol is 75.1% with respect to the stoichiometrical value calculated on the basis of the cumyl phenols present in the feed of phenol pitch; the sum of the recovery yields of cumene and alpha-methylstyrene is 73.6% of the stoichiometrical value calculated on the basis of the cumyl phenols, dimers of alpha-methylstyrene and phenyl dimethylcarbinol present in the phenol pitch fed in.

The pyrolysis residue amounts to 36% by weight with respect to the phenol pitch fed in. The composition in weight percent of said residue is shown in Table 1. The pyrolysis residue has a solification point of 190° C., a high viscosity, and can be removed only with great difficulty.

EXAMPLE 3

In this Example the apparatus used for the thermal decomposition of phenol pitch is a distillation column fitted with 60 plates divided into 45 enrichment plates and 15 stripping plates.

The composition of the phenol pitch used in this Example, expressed in wt.%, is shown in Table 2. The phenol pitch is delivered to the column at a rate of 1400 kg/hour and the steam at a rate of 230 kg/hour. The weight ratio between steam and phenol pitch fed in is thus 0.164:1. The column is operated at a pressure of 7 kg/cm$^2$, with a bottom temperature of the liquid of 360° C. and a temperature of the overhead vapors of 275° C. The vapor phase is discharged from the top of the column at a rate of 898 kg/hour, and the liquid phase is discharged from the bottom at a rate of 732 kg/hour. The average residence time of the phenol pitch in the column is 2 hours.

The composition in weight percent of the overhead product, which contains the useful products recovered together with the water fed in, is shown in Table 2. The recovery yield of phenol is 90.7% of the stoichiometrical value calculated on the basis of the cumyl phenols present in the phenol pitch fed in. The sum of the recovery yields of cumene and alpha-methylstyrene is 104.1% with respect to the stoichiometrical value calculated on the basis of the cumyl phenols, dimers of alpha-methylstyrene and phenyl dimethylcarbinol present in the phenol pitch fed in.

The composition in weight percent of the liquid discharged from the bottom of the column, which constitutes the pyrolysis residue containing the undesired compounds, is shown in Table 2. The pyrolysis residue has a solidification point of 48° C., a sufficient fluidity and is easy to remove.

TABLE 1

| Components | Composition in wt. % of the phenol pitch | Example 1 Composition in wt. % useful products | Example 1 Composition in wt. % pyrolysis residue | Example 2 Composition in wt. % useful products | Example 2 Composition in wt. % pyrolysis residue |
|---|---|---|---|---|---|
| Benzene | — | traces | — | 2.1 | — |
| Acetone | — | 5.95 | — | 0.5 | — |
| Mesityl oxide | — | 0.05 | — | 3.4 | — |
| Diacetone alcohol | — | 0.15 | — | 0.6 | — |
| Cumene | — | 37.8 | — | 32.35 | — |
| Alpha-methylstyrene | — | 14.9 | — | 7.65 | — |
| Phenyl dimethylcarbinol | 5.45 | 0.5 | — | 0.2 | traces |
| Acetophenone | 19.75 | 21.9 | 11.25 | 17.65 | 12.5 |
| Phenol | 2.1 | 17.8 | traces | 17.15 | — |
| o-cumyl phenol | 4.0 | — | 1.4 | — | 0.85 |
| p-cumyl phenol | 22.75 | — | 4.3 | — | 5.85 |
| alpha-methylstyrene dimers | 14.7 | — | 0.7 | — | — |
| other compounds | 31.25 | 0.95 | 82.35 | 18.4 | 80.8 |

TABLE 2

| Components | Composition in wt. % of the phenol pitch | Example 3 Head vapors | Example 3 Bottom liquid |
|---|---|---|---|
| Benzene | — | traces | — |
| Acetone | — | 2.0 | — |
| Mesityl oxide | — | 0.1 | — |
| Methyl isobutyl ketone | — | 0.3 | — |
| Cumene | — | 32.4 | — |
| alpha-methylstyrene | — | 18.8 | — |
| Phenyl dimethylcarbinol | 7.3 | 0.3 | 1.7 |
| Acetophenone | 17.6 | 2.8 | 30.0 |
| Phenol | 2.9 | 17.0 | 0.2 |
| o-cumylphenol | 3.5 | — | 0.6 |
| p-cumylphenol | 16.4 | — | 1.5 |
| alpha-methylstyrene dimers | 13.8 | — | 0.4 |
| other compounds | 38.5 | 0.6 | 65.6 |
| water | — | 25.7 | — |

We claim:

1. A continuous process for treating the phenol pitch obtained as a bottoms fraction in the distillation of raw phenol deriving from the acid hydrolysis of cumene hydroperoxide, to recover therefrom desired products consisting of phenol, alpha-methylstyrene, cumene and acetone, which comprises introducing said phenol pitch, preheated to a temperature of from 180° C. to 280° C., and steam into a reactor in a weight ratio between steam and phenol pitch of from 0.01:1 to 1:1, withdrawing from the top of said reactor a vapor phase comprising said desired products, withdrawing from the bottom of said reactor a liquid phase consisting essentially of compounds with a higher boiling point than said desired products, and operating in the reactor at a pressure of from 4 to 12 $Kg/cm^2$, at a temperature of from 320° to 400° C., as measured in said liquid phase, and with an average residence time of the phenol pitch in the reactor of from 0.5 to 10 hours.

2. The process of claim 1, wherein said weight ratio between steam and phenol pitch is from 0.04:1 to 0.2:1.

3. The process of claim 1, wherein the pressure in the reactor is from 6 to 9 $Kg/cm^2$.

4. The process of claim 1, wherein the reactor is operated at a temperature of from 335° to 370° C., as measured in said liquid phase.

5. The process of claim 1, wherein said average residence time is from 1 to 4 hours.

* * * * *